United States Patent [19]

Newman

[11] 4,195,073
[45] Mar. 25, 1980

[54] RADIOIMMUNOASSAY OF ALPHA$_1$FETOPROTEIN

[75] Inventor: Edward S. Newman, Nutley, N.J.

[73] Assignee: Hoffmann-La Roche Inc., Nutley, N.J.

[21] Appl. No.: 917,814

[22] Filed: Jun. 22, 1978

Related U.S. Application Data

[62] Division of Ser. No. 846,089, Oct. 27, 1977, abandoned.

[51] Int. Cl.$^2$ .................... G01N 33/16; A61K 43/00; C07G 7/00
[52] U.S. Cl. ..................................... 424/1; 260/112 B
[58] Field of Search ............................. 424/1, 12, 177; 260/112 R, 112 B

[56] References Cited

U.S. PATENT DOCUMENTS

| | | | |
|---|---|---|---|
| 3,946,105 | 3/1976 | Nagai et al. | 260/112 B |
| 4,022,877 | 5/1977 | Huber et al. | 424/1 |

OTHER PUBLICATIONS

Ruoslahti et al., Int. J. of Cancer 7, pp. 218–225 (1971).
Alpert et al. J. Biol. Chem. 247, pp. 3492–3498 (1972).
Nishi, Cancer, Res. 30, pp. 2507–2513 (1970).
Nishi et al., Protides Biol. Fluids 18, pp. 43–47 (1971).
Nishi et al., Biochim. Biophys. Acta 278, pp. 293–298 (1972).
Aoyagi et al., Cancer Research 37, pp. 3663–3667 (Oct. 1977).
Yachnin et al., Biochim. Biophys. Acta 493, 418–428 (1977).

*Primary Examiner*—Benjamin R. Padgett
*Assistant Examiner*—Christine M. Nucker
*Attorney, Agent, or Firm*—Jon S. Saxe; George M. Gould; R. Hain Swope

[57] ABSTRACT

A method of isolating alpha$_1$-fetoprotein sufficiently pure to be useful in radioimmunoassay procedures is described. The method comprises the procedures and techniques of affinity chromatography, blue dextran adsorption chromatography and polyacrylamide gel electrophoresis. Wherein a certain degree of reduction in kind and/or quantity of contaminants is not achieved by the first two procedures, gel filtration and mixed ion exchange cellulose chromatography are carried out in preparation for polyacrylamide gel electrophoresis. Monkey alpha$_1$-fetoprotein very similar to human cord blood alpha$_1$-fetoprotein by amino acid composition and physical properties and of sufficient purity to be useful in human radioimmunoassay procedures is obtained by the disclosed method.

4 Claims, No Drawings

RADIOIMMUNOASSAY OF ALPHA₁ FETOPROTEIN

This is a division of application Ser. No. 846,089, filed Oct. 27, 1977, abandoned.

BACKGROUND OF THE INVENTION

A serum protein specific to the fetus was first demonstrated by Pederson, Nature (London) 154, 575 (1944) in calf serum and by Bergstrand et al. Scand. J. Clin. Lab. Invest 8 174 (1956) in humans. This feto-specific protein was designated $alpha_1$-fetoprotein (AFP) due to its electrophoretic mobility. $Alpha_1$-fetoprotein in sera of hepatocellular cancer and malignant embryonal teratoma patients was found to be immunologically and electrophoretically identical with $alpha_1$-fetoprotein observed in fetal serum by Tatarinov, Vopr. Med. Khim. 11 20-24 (1965) and Abelev et al., Int. J. Cancer 2 551-558 (1967).

Human $alpha_1$-fetoprotein has been isolated from fetal serum by chemical procedures by Pederson, Clin. Chimica Acta 38 163-170 (1971), Ruoslahit et al., Int. J. Cancer 7 218-225 (1971), Silver et al., Proc. Nat. Acad. Sci., U.S.A. 70 526-530 (1973), Forrester et al., Clin. Chimica Acta 64 317-323 (1975) and Twomey et al., Clin. Chem. 22 1306-1309 (1976). In addition immunochemical and chemical methods have been employed to isolate $alpha_1$-fetoprotein from hepatoma serum by Nishi, Cancer Res. 30 2507-2513 (1970), Lehmann et al., Clin. Chimica Acta 33 197-206 (1971) and Alpert et al., J. Biol. Chem 247 3492-3497 (1972).

The methods referred to above result in an $alpha_1$-fetoprotein (AFP) which is not pure in that it contains albumin and other proteins. Because of the presence of these contaminants, such relatively impure $alpha_1$-fetoprotein preparations are not satisfactory as the radiolabeled antigen for a sensitive radioimmunoassay. Further, such preparations are not satisfactory for the production of monospecific high titer antisera for a sensitive radioimmunoassay (RIA). Because samples to be tested for AFP in a radioimmunoassay often contain AFP in low concentration, it is essential that the RIA procedure be highly sensitive. By highly sensitive is meant that the RIA must be able to accurately detect AFP at a level of about 20 ng/ml of sample. Such sensitive RIA procedures are required for screening for birth defects in pregant women, which has heretofore not been feasible.

Non-specific antisera or impure labeled AFP cannot be utilized in such sensitive RIA procedures since they would not yield an accurate measure of the AFP content of the sample. In addition, the methods of $alpha_1$-fetoprotein reported in the literature are not satisfactory for isolating AFP from large volumes of source solutions and/or source solutions which contain low concentrations of AFP. Further, the methods disclosed in the literature for isolating AFP do not appear to be satisfactory for automation techniques.

There is thus a need for a method of isolating $alpha_1$-fetoprotein in as pure a state as possible in terms of albumin and other protein contaminants which would interfere with sensitive radioimmunoassays. Further, there is a need for isolating AFP which can be efficiently applied to large volumes of source solutions and/or source solutions which contain AFP in low concentration. Finally, there is a need for a method of isolating AFP which is amenable to being carried out, wholly or partially, by automated apparatus and techniques. These needs are all satisfied by the method of the subject invention. Further, the methodology of the present invention affords a means whereby AFP can be obtained from monkey hepatoma serum in sufficient purity so as to be for practical purposes, the same as that obtained from human cord serum and sufficiently pure to be used in RIA procedures on human samples. Monkey AFP has heretofore not been recognized as being usable in radioimmunoassays on human material.

DESCRIPTION OF THE INVENTION

This invention provides a method for isolating $alpha_1$-fetoprotein from biological source material such as cord blood, hepatoma tissue and extracts thereof, other tumors, ascities fluid, fetal blood, embryonic tissues, amniotic fluid hepatoma blood, and cells grown in culture or in host animals. Further, the present pertains to a method of purifying $alpha_1$-fetoprotein (AFP) from monkey sources, particularly monkey hepatoma blood. It has been found that AFP purified from this source according to the invention demonstrates immunologic identity with AFP present in human cord blood and human ascities fluid. The use of monkey source material such as hepatoma blood for the isolation of pure AFP by the method of the invention is significant because such material is more uniform and significantly higher in AFP content than certain other sources such as human cord blood. AFP concentration in monkey hepatoma blood ranges from about 1 to about 5 mg./ml. as opposed to human cord blood which contains from about 0.06 to about 0.1 mg./ml.

The process of this invention provides a pure $alpha_1$-fetoprotein (AFP) essentially free of albumin and other protein contaminants and which can be used in a sensitive radioimmunoassay. The process involves using the following techniques in sequence:

(a) affinity chromatography on an immunosorbent column;
(b) blue dextran adsorption chromatography;
(c) gel filtration;
(d) mixed ion exchange cellulose chromatography and
(e) polyacrylamide gel electrophoresis.

The resulting product, $alpha_1$-fetoprotein, is homogenous, i.e., appears as a single band, by analytical disc electrophoresis. Upon immunoelectrophoresis, AFP obtained by the method of the subject invention demonstrates an electrohporetic mobility in the $alpha_1$-globulin region, demonstrates a single precipitin line when diffused against a heterospecific anti-AFP serum and will not show a precipitin line against high titered anti-normal human serum or anti-human serum albumin. These observations have been confirmed by radioimmunoelectrophoresis. AFP purified in accordance with the subject invention demonstrates a line of identity in double immunodiffusion with $alpha_1$-fetoprotein in cord serum, hepatocellular cancer serum and ascities fluid and is essentially free of albumin and other proteins which would interfere with its use in sensitive radioimmunoassays (RIAs).

The novel process of this invention involves a combination of immunological, chemical, filtration, electrostatic and electrophoretic methods and techniques.

Affinity Chromatography

In order to remove the bulk of the extraneous proteins from an $alpha_1$-fetoprotein containing sample of source solution such as, for example, human cord serum or monkey hepatoma serum, the sample is initially subjected to affinity chromatography.

Affinity chromatography is an immunological adsorption technique wherein the antigen is removed from solution by being adsorbed onto an immunosorbent which comprises antibodies specific to the antigen to be isolated covalently coupled to a solid, particulate support. Proteins which do not react with the immobilized antibody are not bound to the solid support. These unbound contaminants are therefore easily separated from the bound antigen. The antigen is thereafter separated from the antibody which remains bound to the solid support.

In order to assure that the affinity chromatography is specific to the antigen sought, the immunosorbent must be treated to block the non-specific sites remaining after the antibody is coupled thereon. In order to accomplish this, the immunosorbent formed by coupling the antibody to a solid support is first equilibrated with a suitable buffer. The immunosorbent is then treated sequentially with normal human serum, again with the same buffer utilized to equilibrate and with ammonium thiocyanate. The immunosorbent is then reequilibrated utilizing the same buffer.

After the the immunosorbent is equilibrated, the sample is passed through the column and the antigen, AFP, is adsorbed unto its antibody while extraneous proteins are eluted therefrom. The sample is initially diluted with buffer at pH 7.0 so that a theoretical AFP concentration of from about 0.05 to about 0.1 mg./ml. is obtained. In the case of, for example, cord serum a 1:1 volume dilution is formed with the buffer. After the sample has been passed through the column, the antigen is eluted by use of a desorbing agent which breaks the antigen-antibody complex. Suitable desorbing agents include, for example, 6 to 8 molar solutions of urea, aqueous sodium chloride solutions having a high concentration, i.e., 0.5 molar and above, acid buffers, i.e., buffers having a pH of from about 2 to about 3 and buffers containing chaotropic ions, i.e., ions known to possess the ability to break antigen-antibody bonds such as, for example, the thiocyanate ion. A preferred desorbing agent is 3.0 M ammonium thiocyanate in 0.1 M sodium phosphate buffer at pH 7.0. The desorption of the AFP from the chromatography column regenerates the column which requires only equilibration with a suitable buffer for reuse.

The combined eluates of the adsorbed fraction, i.e., the AFP-containing fraction, are then dialyzed against deionized water and the resulting dialysate concentrated by ultrafiltration. The adsorbed fraction is then tested for AFP content by immunologic techniques.

The materials which are suitable for use as solid supports for the antibody must meet a number of critical parameters, i.e., they must (a) immobilize gamma globulin (antibodies) without adversely affecting their immunological properties,
(b) permit a sample of test fluid to pass through a column at an acceptable rate,
(c) be inert, i.e., they must have no immunologically interfering properties or be capable of being modified chemically or immunologically so as to have no such interfering properties,
(d) permit desorption of antigens without the antibody being desorbed or affected immunologically; and
(e) be suitable for use in an automated system.

Materials which have these properties include, for example, agarose gels, porous glass beads, polyacrylamide beads and the like, preferably, agarose gels. Agarose is the neutral portion of agar. Agarose gel is commercially available, for example, under the trademark "Sepharose" from AB Pharmacia, Uppsala, Sweden. The commercially available agarose gels are aqueous suspensions usually containing a preservative such as, for example, 0.02% sodium azide. The gel is prepared in bead form having a selected particle size and percent concentration of agarose. The concentration of the agarose in the gel determines its fractionation range.

The gels most suitable for use in the affinity chromatography step of this i.e., which meet all of the above-mentioned criteria, are available under the trademark "Sepharose 4B". These gels have a particle size of from 40-190 microns and contain 4% by weight agarose. Further, these gels have a fractionation range of $3 \times 10^5$ to $3 \times 10^6$.

The buffer preferred for use in the affinity chromatography step of this invention is a 0.1 M phosphate buffer at pH 7.0. Other buffers which might be utilized are, for example, borate buffers at pH 8, acetate buffers at pH of about 5 and the like. The choice of a particular buffer is governed by factors as, for example, the stability of the antigen being isolated and the like.

The preferred method of concentrating the dialysate by ultrafiltration is to use a stirred cell containing a membrane having a molecular weight cut off of 10,000, such as a PM-10 membrane available from Amicon Corp., Lexington, Massachusetts. It is also possible to concentrate the dialysate by other methods known in the art such as, for example, freeze drying.

The AFP content in the resulting material can be monitored by several immunological assay means, however, radioimmunoassay (RIA) is preferred. Where feasible, the addition of a small measured amount of radiolabelled AFP to the partially purified sample and the monitoring of its passage through the various stages of the process facilitates and insures the purity of the final preparation.

The affinity chromatography step of the process of this invention can be automated by using a modified version of a device named "CYCLUM" which was developed at Oak Ridge National Laboratory, Oak Ridge, Tennessee. The CYCLUM control panel with its associated equipment is programmed by the use of a cam timer to select one of three liquids to flow through an affinity column, monitor and record the optical density of the effluent and dispense the effluent into one of the three containers. The CYCLUM which has the capacity to continuously recycle the affinity chromatography treatment, is described in Anderson et al., Cancer Research, Vol. 34, pp. 2066 to 2076 (1974).

Blue Dextran Adsorption Chromatography

Albumin present in the adsorbed fraction produced in the previous step is substantially removed from the AFP by means of a Sepharose-blue dextran adsorbent. Sepharose-blue dextran (SBD) is formed by covalently linking blue dextran to agarose, i.e., Sepharose by the method of Nishikawa et al. Anal. Biochemistry, Vol. 64, pp. 268–275 (1975). This involves activating Sepharose, preferably Sepharose 4B, with cyanogen bromide buffered at pH 11 at about 4° C. Blue dextran, i.e., dextran having a blue chromophore chemically bound thereto, is then added in 0.1 M phosphate buffer at pH 7 and the reaction is allowed to proceed for 24 hours at about 4°

C. The chromophore component of blue dextran is a simple derivative of the dye Procion Blue H-B. The molecule contains an aromatic group through which attachment to the activated Sepharose is made. The resulting preparation of agarose gel blue dextran is capable of binding 10 mg. of albumin per ml. of packed gel.

The blue dextran adsorption chromatography is carried out utilizing a column 5 cm × 13 cm. The procedure described in Travis et al., Clin. Chimica Acta 49 49–52 (1973) is used to selectively remove the albumin from the AFP containing fractions. Accordingly, the pooled AFP containing fractions from the affinity column are dialyzed against the column buffer, i.e., 0.05 M TRIS–0.5 M NaCl, pH 8.0, prior to being pumped through the Sepharose-Blue Dextran gel bed. The unadsorbed eluate which contains AFP, is pooled and concentrated by ultrafiltration or other suitable means as in the previous step. The resulting AFP containing material is essentially free of albumin as determined by immunologic techniques. About 90% to 95% of the albumin originally present in the sample is removed by this technique. The Sepharose-blue dextran column may be regenerated by treatment with a 6.0 molar urea solution to remove the albumin, followed by equilibration with a suitable buffer.

Gel Filtration Chromatography

The unadsorbed fraction from the Sepharose-blue dextran column containing AFP is then subjected to gel filtration chromatography to separate the high molecular weight contaminants and a portion of any remaining albumin. The molecular weights of AFP and albumin are 72,000 and 69,000 daltons, respectively. By high molecular weight contaminants is meant proteins having a molecular weight of about 100,000 or more. The preferred column for this treatment contains a filtering material which is a hydrophilic, water-insoluble, cross-linked dextran polymer gel. This material and the method of its manufacture are described in British Pat. No. 854,715. The preferred gel material, which is commercially available from AB Pharmacia, Uppsala, Sweden under the name "Sephadex", comprises a three dimensional macroscopic network of dextran substances bonded or cross-linked together which is capable of absorbing water with swelling. The ability of the gel material to take up water is inversely proportional to the degree of cross-linked of dextran substances in the gel material. The gel material is available in a variety of different grades differing with respect to degree of porosity. The gel preferred for use in this invention has an approximate molecular weight exclusion limit of 200,000, a water regain (g. $H_2O$/g. dry gel) of $20\pm2.0$, a particle size of 40–120 microns and a bed volume/ml./gm. dry gel of 30–40. This particular gel is designated "Sephadex G-200".

The gel column is equilibrated with 0.05 M monobasic sodium phosphate–0.15 M sodium chloride buffer, pH 5.0. The unabsorbed fraction from the Sepharose-blue dextran column, which contains AFP, is concentrated and dialyzed by discontinuous diafiltration against the same buffer and then chromatographed on the equilibrated gel column, using upward flow. Upward flow is used because it facilitates separation of the AFP from low- and high-molecular weight protein contaminants and maintains the integrity of the gel bed.

The eluate from the column is collected in fractions of, e.g., 10 ml. These fractions are monitored for protein content and radioactivity. In addition, the AFP content of certain fractions is confirmed by RIA procedure. Generally, about 150 such fractions are obtained. The fractions having the highest AFP content are collected and pooled. The rest are discarded. Generally, when 150 fractions are collected, fractions 100 to 120 have been found to contain the maximum AFP.

Ion Exchange Cellulose Column Chromatography

In order to further remove contaminating proteins from the AFP-containing fractions from the gel filtration chromatography step, the pooled fractions are subjected to ion exchange cellulose column chromatography. This procedure separates the proteins by virtue of their electrostatic binding capacity as opposed to, e.g., the previously carried out gel filtration chromatography which separated the proteins by size.

The ion exchange column found suitable for use in this procedure is a mixed bed column composed of a cationic exchanger, e.g., carboxymethyl cellulose and an anion exchanger, e.g., diethylaminoethyl cellulose.

The carboxymethyl celluloses suitable for use in this procedure are, for example, those which are microgranular in form, have rod shaped particles with a particle size distribution expressed as the diameter of equivalent spheres within a range of about $20\mu$ to about $a\mu$, have a capacity of $1.0\pm$meq./gm. and a water regain of 2.3–2.7 gm./gm. dry exchanger. The preferred ionic form is the $Na^+$ form. A suitable ion exchanger is commercially available in a dry form from H. Reeve Angel Inc., Clifton, New Jersey, under the trade name "CM 52".

The diethylaminoethyl cellulose preparations most suitable for use in this procedure are those which are microgranular in form, have rod shaped particles with a particle size distribution expressed as the diameter of equivalent spheres within a range of about $20\mu$ to about $60\mu$, have a capacity of $1.0\pm0.1$ meq./gm. have a water regain of 2.3–2.8 gm./gm., dry exchanger and are in the free base form. A suitable ion exchanger, for example, is that commercially available from H. Reeve Angel Inc., Clifton, New Jersey under the trade name "DE 52".

The mixed ion exchange cellulose column is prepared as follows. First, the fines are removed from each exchanger, for example, by aspiration of the supernatant resulting from adding a 10-fold volume of water, stirring and allowing the solids to settle. Second, each exchanger is separately equilibrated with a 2 molar sodium chloride solution in 0.1 M ammonium acetate. After aspiration of the supernatant, a buffer solution of 0.1 M ammonium acetate is added to each of the celluloses and equal volumes of each of the resulting slurries are combined and packed by gravity into a 2.5 cm × 13.0 cm column. The resulting column is equilibrated in terms of the buffer to be used, i.e., 0.1 M ammonium acetate.

The pooled fractions from the gel filtration procedure are concentrated and equilibrated by dialysis against the 0.1 M ammonium acetate buffer. The AFP containing solution is then applied to the ion exchange column at the rate of 60 ml./hr.

After the AFP solution has been applied to the column, the column is washed with additional buffer to remove any material which does not bind thereto. Thereafter, a linear sodium chloride gradient is established by the very gradual addition of sodium chloride to the buffer. As the salt concentration increases in the buffer, 3 ml. fractions are collected and, as in the previous step, monitored for protein content, radioactivity and for AFP by RIA. Again, the AFP containing fractions are collected and pooled.

Preparative Polyacrylamide Electrophoresis

Purification of the AFP is completed by polyacrylamide electrophoresis. This procedure, which separates AFP from contaminating proteins on the basis of differences in molecular charge, size and shape, removes any remaining interfering traces of albumin which might be present. This procedure is carried out preferably utilizing a Buchler Polyslab (Buchler Instruments, Fort Lee, New Jersey) which is a verticle 170 mm×3.0 mm slab of a 7% polyacrylamide resolving gel having a 10 mm×3.0 mm concentrating gel polymerized on top of the resolving gel.

The difference between the concentrating gel and resolving gel described above is basically pore size, the former being larger. Variance in pore size is achieved by varying the relative proportions of monomer, i.e., acrylamide and comonomer (crosslinking agent), i.e., N,N'-methylenebisacrylamide in the polymerization mixture. For a description of these gels, their preparation and use thereof in electrophoretic procedures, see Davis, "Disc Electrophoresis - II, Method and Application to Human Serum Proteins". Annal. N.Y. Acads. Sci., Vol. 121, pp. 404–427 (1964).

The collected, pooled fractions from the previous procedure are dialyzed against water. The dialysate is then lyophilized to a powder. The powder is then dissolved in a small quantity of a buffer termed electrophoresis buffer. This buffer solution contains about 0.6% by weight TRIS, i.e., 2-amino-2-(hydroxymethyl)-1,3-propanediol and about 3% by weight glycine with a pH of approximately 8.3. Sucrose and a trace of a suitable dye such as, for example, bromophenol blue are then added to the sample. The bromophenol blue is used as an indicator of the progress of the procedure as it migrates through the gels ahead of the proteins. The sucrose is present to increase the density of the sample solution somewhat. It is preferred to add sufficient sucrose to achieve a concentration of about 8% by weight. The AFP containing solution is placed into the Buchler Polyslab and electrophoresis is carried out for 24 hours at 40 mA constant current. During electrophoresis, the proteins in the layer of sample solution which is 4–6 mm. in height will first form a thin band, i.e., about 1 mm. in height, near the bottom of the concentrating gel before migrating through the resolving gel layer.

When electrophoresis is complete, the resolving gel is removed and sliced to 0.5 cm thick strips transverse to the path between the cathode and the anode. The strips are individually eluted with 0.05 M borate buffer at pH 8.4. The eluates of the strips are monitored for AFP content by radioactivity, double immunodiffusion and RIA.

The above-described five step process is required in accordance with the present invention to obtain pure AFP from certain sources such as human cord serum. It is within the purview of the present invention, however, to obtain pure AFP from other sources, particularly monkey hepatoma serum utilizing only three of the five described steps. The choice between these three steps, i.e., affinity chromatography, blue-dextran adsorption chromatography and polyacrylamide electrophoresis, and the above described five step procedure is made in view of the following considerations.

The choice of a three step vs. a five step procedure for obtaining pure AFP in accordance with the present invention is to be made in consideration of the nature and/or the quantity of contaminants. The determination of whether three or five steps are required is made after the blue dextran chromatography is carried out. A sample of the pooled unabsorbed fractions from blue dextran chromatography is subjected to analytical disc electrophoresis. If this procedure demonstrates contaminants of 20% and above, the five step procedure is utilized. Even if the level of contaminants is within acceptable limits, i.e., less than 20%, a five step procedure is nonetheless utilized if the contaminants demonstrate an electrophoretic mobility similar to that of AFP.

In the event that only a three step purification procedure is required, the pooled, unadsorbed fractions from the blue dextran chromatography are dialyzed and lyophilized. The resulting powder is then dissolved in the electrophoresis buffer and subjected to polyacrylamide electrophoresis as described above.

The above-described process, regardless of whether three or five steps are utilized, yields pure AFP as judged by analytical disc electrophoresis. The pure AFP obtained from e.g., cord serum, ascites fluid and hepatoma serum, demonstrates immunologic identity in immunodiffusion. AFP obtained from monkey hepatoma serum likewise demonstrated immunologic identity with the preparations obtained from human sources. The observation of a single precipitin line in immunodiffusion for these preparations of purified AFP against a heterospecific unabsorbed rabbit anti-AFP serum demonstrated immunologic homogeneity. The purity of AFP obtained in accordance with the method of the present invention was also determined by immunoelectrophoresis of the purified AFP against anti-AFP serum (one precipitin line) and high titered anti-normal human serum anti-human serum albumin (no precipitin line).

The purity of the AFP obtained in accordance with the subject invention was determined, in addition to the methods previously mentioned, by specific activity. The specific activity equals the antibody neutralization (RIA) divided by the protein concentration and is described by Lowry et al., J. Biol. Chem., Vol. 193, pp. 265–275 (1951). Bovine serum albumin (Pentex, Cat. No. 83–301) was used as the protein reference standard. The specific activity of the purified AFP prepared in accordance with the present invention was found to range between 0.87 and 0.95 for cord serum AFP and between 0.94 and 0.99 for hepatocellular carcinoma serum AFP. In contrast, the specific activity of the AFP containing pooled fractions prior to preparative polyacrylamide electrophoresis ranged from 0.45 to about 0.75 and yielded a radiolabeled product which was not usable in a RIA procedure due to large amounts of iodinated high and low molecular weight contaminants.

The purified AFP prepared in accordance with the subject invention is suited for use in a highly sensitive diagnostic radioimmunoassay for hepatocellular cancer and birth anomalies. AFP previously known to the art is not well suited to such a radioimmunoassay procedure because of the amount of albumin present. In addition to facilitating the substantial removal of albumin which interferes with sensitive RIA procedures, the method of the present invention is advantageous over other attempts to purify AFP known to the art in that it is effective in isolating AFP from solutions which contain it in low concentration and, further, that it is effective because of automation in dealing with large volumes of such solutions. Further, the method of the subject invention provides AFP isolated from monkey hepatoma serum of such purity that it is very similar to AFP obtained from human sources by amino acid analysis and is usable in RIA procedures in place of AFP from human sources.

For use in radioimmunoassay procedures, AFP particularly monkey AFP is radiolabeled with radioactive atoms which will react with its chemically reactive groups and not substantially diminish its antigenicity. $^{125}$I has been found to be particularly suitable. AFP can be radioiodinated by methods known in the art, with minor modifications to concentration and volume. The Chloramine T method of Hunter and Greenwood described in J. Biochem 91, 46 (1964) using iodine 125 is particularly useful.

The reaction is effected, for example, by mixing 50 μg. AFP in borate buffer with 5mCi of Na$^{125}$I (pH 8–11) and 100 μg. fresh Chloramine T (sodium p-toluenesulfochloramine) all in borate buffer. The reaction takes place in 1 minute at room temperature and is stopped by the addition of sodium metabisulfite. The labeled product is mixed with 1 ml. of a 5% human serum albumin solution and the mixture applied to a cross-linked dextran gel column, e.g., Sephadex G-100, to separate the product from unreacted $^{125}$I. The product is then eluted from the column with, e.g., 0.1 M TRIS-0.15 M sodium chloride buffer, pH 7 and collected in tubes (5 ml. fractions) containing 0.5 ml. of a 5% human albumin solution. The product is diluted to suitable concentration with borate buffer containing 0.25% human albumin.

The monkey AFP labeled with $^{125}$I as described above is particularly suited to a radioimmunoassay procedure. That one skilled in the art would not appreciate that this material could be so utilized is evident when it is considered that, prior to the present invention, AFP had not been prepared sufficiently pure for RIA procedures and, further, that the prevailing feeling among those skilled in the art has been that only materials of human origin could be used as the labeled source material for the quantitative assay of human AFP by RIA. AFP purified in accordance with the present invention can be used in a highly sensitive radioimmunoassay for AFP, i.e., a sensitivity of from about 0.5 ngm. to about 18 ngm.

A preferred RIA utilizing AFP purified in accordance with the present invention is a solid phase immobilized second antibody procedure. In this procedure rabbit anti-AFP is the primary antibody and goat antiserum, i.e., goat anti-rabbit gamma globulin as the secondary antibody. The standard material for the assay is partially purified cord blood AFP.

In conducting the radioimmunoassay, a standard competitive-inhibition curve is created. It is a measure of the complex formation between the added antigen with specific antibodies. The curve reflects the amount of AFP per unit of sample. The measurement is in nanograms per dose per aliquot of standard AFP solution which is plotted against the quantity of antibody complexed with radiolabeled pure AFP. The resulting curve is used to determine the amount of AFP in a sample, i.e., serum, plasma or amniotic fluid.

In a preferred method, a measured standard material is added to a series of tubes containing ethylenediaminetetraacetic acid (EDTA) buffer, pH about 6 which contains about 1% by volume normal goat serum. A measured amount of primary antibody, i.e., rabbit anti-AFP, diluted with a suitable buffer such as, for example, 0.05 M borate buffer, pH 8.4 containing 0.25% by weight human albumin.

Following the addition of dilute antibody, a measured amount of radioiodinated pure monkey AFP, is added to each tube. The amount added can, for example, range between 0.6 ng. and 1.0 ng. The resulting solutions are incubated at ambient temperature for a sufficient time to complete the reaction, usually about 5 hours. When the incubation is completed, the immobilized secondary antibody, i.e., goat anti-rabbit gamma globulin, is added to each tube and the solution again incubated for an additional period of about 5 minutes at ambient temperature. The immobilized antibody complexes with the AFP/primary antibody complex thereby facilitating its removal from solution.

Under the conditions described above, free AFP remains in solution. The $^{125}$I content of the precipitate or the supernatant is then determined on a suitable counter and the radioactivity then can be plotted against the antigen concentration. In this way a curve is established which can be utilized to determine the amount of AFP in a sample of plasma, serum or amniotic fluid following the procedure described above.

The secondary antibody can be immobilized by a number of means recognized in the art such as, for example, by the methods previously described with reference to immunosorbent. In addition to beads, glass or polycarbonate rods are also suitable for immobilizing the second antibody. A preferred method of immobilizing the secondary antibody is to adsorb it onto an unsintered fluorocarbon polymer according to the method described in Fishman, U.S. Pat. No. 3,843,443 issued Oct. 22, 1974. A particularly preferred fluorocarbon polymer for immobilizing the secondary antibody is unsintered polyvinylidene fluoride.

It is to be understood that the present invention insofar as it pertains to improvements in RIA procedures is not intended to be limited to the procedure described above. Any radioimmunoassay procedure recognized in the art for AFP comprising, basically, forming a complex of the AFP in an unknown with an antiserum, adding thereto a probe, i.e., radiolabeled AFP, removing the resulting complex from solution and measuring the amount of radiolabeled material taken up against a standard can be improved by using as the radiolabeled material purified AFP prepared in accordance with the present invention.

The accuracy of the RIA is dependent on the purity of the radiolabeled material. Because radioimmunoassays for AFP such as described above are rendered more sensitive utilizing AFP purified in accordance with the present invention, they can now be utilized, for example, in a screening program for birth defects in pregnant woman. The use of an RIA procedure in such a program has heretofore not been considered feasible.

The following Examples further illustrate the invention.

EXAMPLE 1

Pooled human cord blood serum was obtained from term pregnancies and stored at −20° C. The serum was thawed, centrifuged at 100,000 r.p.m. for 1 hour at 4° C. and the supernatant fluid diluted with an equal volume of 0.1 M sodium phosphate buffer containing 0.02% by weight sodium azide, pH 7.0.

Affinity Chromatography

Portions of 15 ml. of the dilute cord serum prepared above were cycled through an automated recycling chromatographic system programed to dispense three liquids, i.e., sample, buffer and desorbent into an affinity column and separately collect waste, unadsorbed fraction and adsorbed fraction. The process was repeated continuously until all of the diluted cord serum had been chromatographed through the column. The adsorbed fractions were collected and dialyzed against deionized water by passage through two Bio-Rad Hollow Fiber Units (Bio-Rad, Cat. # B/HDG-1) connected in series. The dialysate was pooled and concentrated to a volume of about 20 ml. by ultrafiltration.

The column of the automated chromatographic system was packed with an immunosorbent prepared as follows:

Alpha$_1$-fetoprotein was isolated from the serum of a monkey with a chemically induced hepatoma. The AFP was purified by affinity chromatography and ascending gel filtration column chromatography and equilibrated with 0.05 M monobasic sodium phosphate–0.15 M sodium chloride buffer at pH 5.0. New Zealand white rabbits were immunized with the antigen which had been coupled to methylated bovine serum albumin prior to mixing with complete Freund's adjuvant. The production of high titer anti-AFP serum was monitored by double immunodiffusion and immunoelectrophoresis.

The rabbit anti-AFP (monkey) serum thus produced was absorbed with 3 mg./ml. of powdered human serum albumin for 1 hour at 37° C. followed by 18 hours at 4° C. and centrifugation at 100,000 r.p.m. for 1 hour. The resulting 30 ml. of adsorbed antibody was subjected to descending DEAE cellulose column chromatography on a 2.5 cm×40.0 cm column in 0.01 M sodium phosphate buffer at pH 8.0. The antibody-containing fractions were pooled and covalently linked to 50 ml. of Sepharose 4B (Pharmacia) activated with cyanogen bromide dissolved in N-methyl-2-pyrrolidone. The gamma globulin fraction was added to the activated Sepharose 4B and the reaction was allowed to proceed for 24 hours at 4° C. After mixing with an equal volume of aqueous 1 M ethanolamine for one hour at pH 8.0, the immunosorbent was equilibrated in 0.1 M sodium phosphate buffer at pH 7.0 and packed into a 5.0×30.0 cm chromatographic column equipped with sliding flow adaptors to a height of 6 cm. To prevent nonspecific adsorption of protein, the immunosorbent was treated by the sequential addition of 20 ml. of normal serum, 0.1 M phosphate buffer at pH 7.0, 3.0 M ammonium thiocyanate in 0.1 M phosphate buffer at pH 7.0 and finally reequilibrated with 0.1 M phsophate buffer, pH 7.0.

Blue Dextran Adsorption Chromatography

Sepharose-blue dextran was prepared by covalently linking Blue Dextran 2000 (Pharmacia) to Sepharose 4B. The product was packed into a 5 cm×13 cm column. The sample from the affinity chromatography procedure was pumped through the column at the rate of 120 ml./hr. to remove most of the albumin present. Fractions of 10 ml. were collected. The gel bed was washed free of unabsorbed protein. A solution of 6 M urea in the column buffer, i.e., 0.05 M TRIS, i.e., 2-amino-2-(hydroxy-methyl)-1,3-propanediol, and 0.05 M sodium chloride was utilized to desorb the albumin from the column thereby regenerating it. The AFP-containing fractions of the unadsorbed eluate were pooled and concentrated by ultrafiltration. To insure total removal of the albumin, the unabsorbed fraction was rechromatographed on the column. The column was again regenerated as described above.

In this step and in subsequent steps, the purification of AFP was monitored by analytical disc electrophoresis and by immunologic techniques, e.g., immunoelectrophoresis, double immunodiffusion and RIA.

Gel Filtration Chromatography

The unadsorbed fraction from the Sepharose-blue dextran column was concentrated and dialyzed to a volume of approximately 20 ml. by discontinuous diafiltration against 0.05 M monobasic sodium phosphate–0.15 M sodium chloride buffer, pH 5.0. The dialyzed sample was chromatographed to remove high molecular weight contaminants by passage through a 5.0 cm×85.0 cm column packed with Sephadex G-200 (Pharmacia), previously equilibrated with the phosphate saline buffer described above, at an upward flow rate of 60 ml./hr. The eluate from the column was collected in 10 ml. fractions. The fractions (150 in all) were monitored for protein content and radioactivity. Fractions 100 through 120, which were found to have the highest AFP content, were collected and the rest discarded.

Ion Exchange Cellulose Chromatography

A mixed bed cationic exchanger (carboxymethyl cellulose)/anionic exchanger (diethylaminoethyl cellulose) medium was equilibrated with 0.1 M ammonium acetate at pH 6.25 and gravity packed into a 2.5 cm×13.0 cm column. The pooled fractions from the previous procedure were equilibrated with the ammonium acetate buffer and applied to the column at a flow rate of 60 ml./hr. After addition of the pooled fractions was complete, 150 ml. of pure buffer were applied to the column. Thereafter a linear salt gradient was established by gradually increasing the proportion of a buffer of 0.5 M sodium chloride in 0.1 M ammonium acetate at pH 6.25 in the stream of pure buffer. As the proportion of salt in the buffer flow increases, proteins are removed from the column in accordance with their electrostatic binding capacity. Fractions of 3 ml. were collected and monitored for protein content and radioactivity as in the previous procedure. The AFP-containing fractions were collected and pooled.

Preparative Acrylamide Electrophoresis

The pooled fractions from the preceding step were dialyzed against deionized water and lyophilized. The resulting powder was dissolved in 2.0 ml. of a mixture of 1 part of a 40% by weight aqueous solution of sucrose containing a trace of bromophenol blue and 3 parts of electrophoresis buffer which contains in each liter 6.0 g. TRIS, i.e., 2-amino-2-(hydroxymethyl)-1,3-propanediol, and 28.8 g. glycine, pH 8.3.

A Buchler Polyslab (Buchler Instruments, Inc.) which comprises a verticle 170 mm×3.0 mm slab of 7% polyacrylamide resolving gel (small pore) on top of which is a 10 mm×3.0 mm polyacrylamide concentrating gel (large pore) was equilibrated with the electrophoresis buffer. The solution containing the sample was loaded onto the Polyslab and put under a constant current of 40 mA for 24 hours. During electrophoresis, the proteins in the sample initially collected as a fine line in the concentrating gel, then gradually dispersed and separated in the resolving gel due to differences in molecular weight, size and charge.

After electrophoresis was completed, the resolving gel was sliced into 0.5 cm wide slices transverse to a path between the cathode and the anode. The slices were then eluted with 0.05 M borate buffer, pH 8.4. The eluates were monitored for radioactivity and AFP content by double immunodiffusion and RIA techniques. The eluates containing highly purified AFP were concentrated by ultrafiltration to approximately 3 ml.

EXAMPLE 2

Individual serum samples obtained from monkies having a chemically induced hepatoma were stored at $-20°$ C. The AFP concentration of the samples was determined to be in the range of 0.6 to 3.2 mg./ml. by RIA procedure. The samples were thawed and centrifuged at 100,000 r.p.m. for 1 hour. Taking the maximum value obtained by RIA as a basis, the supernatant was diluted to a content of 0.08 mg AFP/ml. with 0.1 M sodium phosphate buffer containing 0.02% by weight sodium azide, pH 7.0.

Ten ml. portions of the diluted monkey serum (containing a total of 0.8 mg. AFP-RIA activity) were cycled through an automated recycling chromatographic system in accordance with the procedure of Example 1. The adsorbed fractions were concentrated and then chromatographed through a Sepharose-blue dextran adsorbent column in accordance with the procedure of Example 1.

The unadsorbed fraction from the Sepharose-blue dextran procedure was dialyzed and lyophilized. The resulting powder was dissolved in 2.0 ml. of the sucrose-bromophenol blue-electrophoresis buffer as described in Example 1 and subjected to preparative polyacrylamide electrophoresis. The eluates were concentrated by ultrafiltration to yield 3 ml. containing highly purified AFP. Specific activity greater than 0.94 was achieved.

I claim:

1. In a radioimmunoassay to determine the alpha$_1$-fetoprotein content in an unknown comprising: forming a complex of the alpha$_1$-fetoprotein in said unknown with an antiserum; adding thereto radiolabeled alpha$_1$-fetoprotein; removing the resulting complex from solution; and measuring the amount of radiolabeled alpha$_1$-fetoprotein taken up in said complex against a standard, the improvement which comprises adding to said first complex radiolabeled alpha$_1$-fetoprotein purified by a process comprising:
   (a) buffering a sample of a biological source material known to contain alpha$_1$-fetoprotein to a pH of about 7;
   (b) subjecting said buffered sample to affinity chromatography by passage through a column containing an antibody specific for alpha$_1$-fetoprotein immobilized on a solid support and subsequently eluting the bound alpha$_1$-fetoprotein by treatment of the column with a suitable desorbing agent;
   (c) removing substantially all of the albumin present in the eluate from step (b) by subjecting it to adsorption chromatography by passage through a column containing an adsorbent comprising an agarose gel covalently linked to dextran containing a blue chromophore;
   (d) dialyzing the unabsorbed alpha$_1$-fetoprotein-containing solution from step (c);
   (e) removing high molecular weight protein contaminants from the dialyzed solution from step (d) by subjecting it to gel filtration chromatography utilizing as the filtering material a hydrophilic, water-insoluble, cross-linked dextran polymer gel;
   (f) treating the eluate containing alpha$_1$-fetoprotein from step (e) to remove protein contaminants by subjecting it to ion exchange chromatography utilizing as the filtering material a mixture of a cationic exchange resin and an anionic exchange resin;
   (g) dialyzing the eluate containing alpha$_1$-fetoprotein from step (f);
   (h) lyophilizing the dialyzed solution from step (g);
   (i) disolving the powder formed in step (h) in a suitable buffer and subjecting the resulting to polyacrylamide gel electrophoresis.

2. In a radioimmunoassay to determine the alpha$_1$-fetoprotein content in an unknown comprising; forming a complex of the alpha$_1$-fetoprotein in said unknown with an antiserum; adding thereto radiolabeled alpha$_1$-fetoprotein; removing the resulting complex from solution; and measuring the amount of radiolabeled alpha$_1$-fetoprotein taken up in said complex against a standard, the improvement which comprises adding to said first complex radiolabeled alpha$_1$-fetoprotein purified by a process comprising:
   (a) buffering a sample of a biological source material known to contain alpha$_1$-fetoprotein to a pH of about 7;
   (b) subjecting said buffered sample to affinity chromatography by passage through a column containing an antibody specific for alpha$_1$-fetoprotein immobilized on a solid support and subsequently eluting the bound alpha$_1$-fetoprotein by treatment of the column with a suitable desorbing agent;
   (c) removing substantially all of the albumin present in the eluate from step (b) by subjecting it to adsorption chromatography by passage through a column containing an adsorbent comprising an agarose gel covalently linked to dextran containing a blue chromophore;
   (d) dialyzing the unabsorbed alpha$_1$-fetoprotein-containing solution from step (c);
   (e) lyophilizing the dialyzed solution from step (d);
   (f) dissolving the powder formed in step (e) in a suitable buffer and subjecting the resulting solution to polyacrylamide gel electrophoresis.

3. The improved radioimmunoassay according to claim 1 wherein said source material is cord blood or cord serum.

4. The improved radioassay according to claim 2 wherein said monkey source material is monkey hepatoma serum.

* * * * *